(12) United States Patent
Murugesan et al.

(10) Patent No.: US 6,271,248 B1
(45) Date of Patent: Aug. 7, 2001

(54) SUBSTITUTED BIPHENYSULFONAMIDE ENDOTHELIN ANTAGONISTS

(75) Inventors: Natesan Murugesan, Princeton Junction, NJ (US); Joel C. Barrish, Holland; John Lloyd, Yardley, both of PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/488,506

(22) Filed: Jan. 20, 2000

Related U.S. Application Data

(62) Division of application No. 08/728,238, filed on Oct. 8, 1996, now Pat. No. 6,080,774.
(60) Provisional application No. 60/007,032, filed on Oct. 11, 1995.

(51) Int. Cl.[7] .................. A61K 31/42; A61K 31/423; A61P 9/08; C07D 261/14; C07D 263/54

(52) U.S. Cl. .................. 514/375; 514/378; 514/380; 548/221; 548/245; 548/246; 540/484; 546/184; 546/348

(58) Field of Search ................ 548/221, 245, 548/246, 240; 514/375, 378, 380

(56) References Cited

U.S. PATENT DOCUMENTS

| | | | |
|---|---|---|---|
| 2,888,455 | 5/1959 | Kano et al. | 260/239.9 |
| 4,415,496 | 11/1983 | Harris et al. | 260/239.3 |
| 4,661,479 | 4/1987 | Wyvratt, Jr. et al. | 424/258 |
| 5,236,928 | 8/1993 | Chakravarty et al. | 548/335 |
| 5,270,313 | 12/1993 | Burri et al. | 544/327 |
| 5,292,740 | 3/1994 | Burri et al. | 544/310 |
| 5,378,715 | 1/1995 | Stein et al. | 548/263 |
| 5,464,853 | 11/1995 | Chan et al. | 548/243 |
| 5,514,691 | 5/1996 | Chan et al. | 548/243 |
| 5,514,696 | 5/1996 | Murugesan et al. | 548/243 |
| 5,571,821 | 11/1996 | Chan et al. | 548/243 |
| 5,591,761 | 1/1997 | Chan et al. | 548/243 |
| 5,594,021 | 1/1997 | Chan et al. | 548/243 |
| 5,612,359 | 3/1997 | Murugesan | 548/243 |
| 5,780,473 | 7/1998 | Murugesan et al. | 544/335 |
| 5,827,869 | 10/1998 | Murugesan | 514/374 |
| 5,846,985 | 12/1998 | Murugesan | 548/245 |
| 5,846,990 | 12/1998 | Murugesan et al. | 548/235 |
| 5,856,507 | 1/1999 | Polniaszek et al. | 548/241 |
| 5,939,446 | 8/1999 | Murugesan et al. | 544/238 |
| 5,965,732 | 10/1999 | Hunt | 544/224 |

FOREIGN PATENT DOCUMENTS

| | | |
|---|---|---|
| 34011-93 | 9/1993 | (AU) . |
| 67357/94 | 1/1995 | (AU) . |
| 48039/96 | 9/1996 | (AU) . |
| 0364506 | 11/1962 | (CH) . |
| 1059459 | 6/1959 | (DE) . |
| 76072 | 4/1983 | (EP) . |
| 194548 | 9/1986 | (EP) . |
| 404525 | 12/1990 | (EP) . |
| 443983 | 8/1991 | (EP) . |
| 510526 | 10/1992 | (EP) . |
| 526708 | 2/1993 | (EP) . |
| 558258 | 9/1993 | (EP) . |
| 569193 | 11/1993 | (EP) . |
| 601386 | 6/1994 | (EP) . |
| 617001 | 9/1994 | (EP) . |
| 626174 | 11/1994 | (EP) . |
| 633259 | 1/1995 | (EP) . |
| 634175 | 1/1995 | (EP) . |
| 640596 | 3/1995 | (EP) . |
| 682016 | 11/1995 | (EP) . |
| 702012 | 3/1996 | (EP) . |
| 725067 | 8/1996 | (EP) . |
| 749964 | 12/1996 | (EP) . |
| 804036 | 11/1958 | (GB) . |
| 0897440 | 5/1962 | (GB) . |
| 1473433 | 5/1977 | (GB) . |
| 2228933 | 9/1990 | (GB) . |
| 91/15479 | 10/1991 | (WO) . |
| 93/08799 | 5/1993 | (WO) . |
| 93/10094 | 5/1993 | (WO) . |
| 93/23404 | 11/1993 | (WO) . |
| 94/27979 | 12/1994 | (WO) . |
| 95/26957 | 10/1995 | (WO) . |
| 96/31492 | 10/1996 | (WO) . |
| 96/40681 | 12/1996 | (WO) . |

OTHER PUBLICATIONS

S. Norio et al., Chemical Abstracts, vol. 70, No. 19, (1969), 87639g.
T. Saito, Chemical Abstracts, vol. 73, No. 23 (1970), 120511w.
Derwent Abstract No. 88–289069/41 Feb. 27, 1987.
Derwent Abstract No. 88–195835/28 Nov. 26, 1986.
Derwent Abstract No. 88–061295/09 Jul. 9, 1986.
Derwent Abstract No. 87–152485/22 Oct. 11, 1985.
Derwent Abstract No. 62299 E/30 Dec. 11, 1980.
Derwent Abstract No. 40927 D/23 Sep. 11, 1979.
Derwent Abstract No. 91–254550/35 Feb. 19, 1990.
Derwent Abstract No. 86–246709/38 Nov. 27, 1985.
Derwent Abstract No. 35012 K/15 Sep. 24, 1981.

(List continued on next page.)

*Primary Examiner*—Richard L. Raymond
*Assistant Examiner*—Venkataraman Balasubramanian
(74) *Attorney, Agent, or Firm*—Ronald S. Hermenau

(57) ABSTRACT

Compounds of the formula

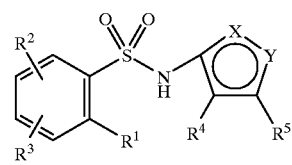

wherein X, Y, $R^1$, $R^2$, $R^3$, $R^4$ and $R^5$ are as described herein, inhibit the activity of endothelin.

25 Claims, No Drawings

OTHER PUBLICATIONS

Allen et al., "Preparation . . . antagonists", CA116(11):106284Z, p. 778, 1992.

R.D. Desai et al., Chemical Abstracts, vol. 71, No. 11, (1969) 49825c.

R.D. Desai et al., Chemical Abstracts, vol. 71, No. 3, (1969) 12872q.

P. G. Ferrini et al., Angew. Chem. Internat. Edit., vol. 2, No. 2 (1963) p. 99.

A. M. van Leusen, et al., "Synthesis . . . Compounds", J. Org. Chem., vol. 41, No. 4, (1976), pp. 69–71.

W. J. Hammar et al., J. Heterocyclic Chem., vol. 18, (1981) pp. 885–888.

A. M. van Leusen et al., Tetrahedron Letters, No. 23, (1972), pp. 2369–2372.

Chan et al., "Identification of a New Class of $ET_A$ Selective Endothelin Antagonists by Pharmacophore Directed Screening", Biochemical and Biophysical Research Communications, vol. 201, No. 1, May 30, 1994, pp. 228–234.

Stein et al., "The Discovery of Sulfonamide Endothelin Antagonists and the Development of the Orally Active $ET_A$ Antagonist 5-(Dimethylamino)-N-(3, 4-dimethyl-5-isoxazolyl)-1-naphthalenesulfonamide", J. Med. Chem., vol. 37, No. 3, Feb. 4, 1994, pp. 329–331.

Doherty, J. Med. Chem., 35(9), 1493–1508 (May 1992).

CA 65: 2241d (1966).

CA 92:41908v (1979).

Wang et al., "Nitrile . . . sinomin," CA 108:94444w, p. 651 (1988).

Khanna, "Oral . . . formulation," CA 115:35728p, p. 415 (1991).

Stein et al., "The Discovery . . . 1-naphthalenesulfonamide," CA 120:18233n, pp. 21–22 (1994).

Vree et al., "Renal excretion . . . function," CA 97:84685r, p. 23 (1982).

Oie, "Pharmacokinetics . . . dosing," CA102:197512x, p. 18 (1985).

Murugesan et al., "N-(heteroaryl) . . . antagonists," CA 120:270370c, p. 1067 (1994).

SUBSTITUTED BIPHENYSULFONAMIDE ENDOTHELIN ANTAGONISTS

This application is a divisional application of U.S. application Ser. No. 08/728,238 filed Oct. 8, 1996 which is now U.S. Pat. No. 6,080,774, which claims priority from provisional U.S. application Ser. No. 60/007,032 filed Oct. 11, 1995.

FIELD OF THE INVENTION

This invention relates to endothelin antagonists useful, inter alia, for treatment of hypertension.

BRIEF DESCRIPTION OF THE INVENTION

Compounds of the formula

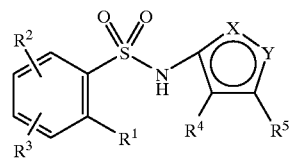

I its enantiomers and diastereomers, and pharmaceutically acceptable salts thereof are endothelin receptor antagonists useful, inter alia, as antihypertensive agents. Throughout this specification, the above symbols are defined as follows:

one of X and Y is N and the other is O;

$R^1$ is

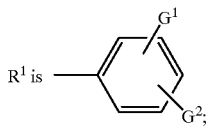

$R^2$ and $R^3$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O)$R^6$;
(h) —CO$^2$H or —CO$_2R^6$;
(i) —SH, —S(O)$_nR^6$, —S(O)$_m$—OH, —S(O)$_m$—O$R^6$, —O—S(O)$_m$—$R^6$, —O—S(O)$_m$OH or —O—S(O)$_m$—O$R^6$;
(j) —$Z^4$—N$R^7R^8$; or
(k) —$Z^4$—N($R^{11}$)—$Z^5$—N$R^9R^{10}$;
$R^4$ and $R^5$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O)$R^6$;
(h) —CO$_2$H or -C$_2R^6$;
(i) —SH, —S(O)$_nR^6$, —S(O)$_m$—OH, —S(O)$_m$—O$R^6$, —O—S(O)$_m$—$R^6$, —O—S(O)$_m$OH or —O—S(O)$_m$—O$R^6$;
(j) —$Z^4$—N$R^7R^8$;
(k) —$Z^4$—N($R^{11}$)—$Z^5$—N$R^9R^{10}$; or
(l) $R^4$ and $R^5$ together are alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^6$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;

$R^7$, $R^8$, $R^9$, $R^{10}$ and $R^{11}$ are each independently
(a) hydrogen; or
(b) alkyl, cycloalkyl, cycloalkylalkyl, cycloalkenylalkyl, aryl or aralkyl, any of which may be substituted with $Z^1$, $Z^2$ and $Z^3$;

$R^7$ and $R^8$ together may be alkylene or alkenylene, either of which may be substituted with $Z^1$, $Z^2$ and $Z^3$, completing a 3- to 8-membered saturated or unsaturated ring together with the nitrogen atom to which they are attached;

any two of $R^9$, $R^{10}$ and $R^{11}$ together may be alkylene or alkenylene, either of which may be substituted with $Z^1$, $Z^2$ and $Z^3$, completing a 3- to 8-membered saturated or unsaturated ring together with the atoms to which they are attached;

$G^1$ is
(a) hydrogen; or
(b) alkyl;

$G^2$ is
(a) hydroxyalkyl;
(b) -(CH$_2$)$_m$O$R^6$; or
(c) -(CH$_2$)$_m$-N$R^{12}R^{13}$;
(d) mono-to hexa-halo substituted alkyl (i.e., alkyl substituted with one, two, three, four, five or six halogen atoms); or
(e) -(CH$_2$)$_n$O$R^{14}$;

$R^{12}$ and $R^{13}$ are each independently
(a) hydrogen; or
(b) alkyl, cycloalkyl, cycloalkylalkyl, cycloalkenylalkyl, aryl or aralkyl, any of which may be substituted with $Z^1$, $Z^2$ and $Z^3$; or P $R^{12}$ and $R^{13}$ together may be alkylene or alkenylene, either of which may be substituted with $Z^1$, $Z^2$ and $Z^3$, completing a 3- to 8-membered saturated or unsaturated ring together with the nitrogen atom to which they are attached, or, together with the nitrogen atom to which they are attached form

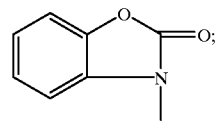

$R^{14}$ is lower alkyl substituted with 1, 2 or 3 halogen atoms;

$Z^1$, $Z^2$ and $Z^3$ are each independently (a) hydrogen;

(b) halo;

(c) hydroxy;

(d) alkyl;

(e) alkenyl;

(f) aralkyl;

(g) alkoxy;

(h) aryloxy;

(i) aralkoxy;

(j) —SH, —S(O)$_n$Z$^6$, —S(O)$_m$—OH, —S(O)$_m$-OZ$^6$, —O—S—(O)$_m$-Z$^6$, -O-S(O)$_m$OH or —O—S(O)$_m$-OZ$^6$;

(k) oxo;

(l) nitro;

(m) cyano;

(n) —C(O)H or —C(O)Z$^6$;

(o) —CO$_2$H or —CO$_2$Z$^6$;

(p) —Z$^4$-NZ$^7$Z$^8$;

(q) —Z$^4$-N(Z$^{11}$)-Z$^5$-H;

(r) —Z$^4$-N(Z$^{11}$)-Z$^5$-Z$^6$; or (s) —Z$^4$-N(Z$^{11}$)-Z$^5$-NZ$^7$Z$^8$;

Z$^4$ and Z$^5$ are each independently (a) a single bond;

(b) —Z$^9$—S(O)$_n$-Z$^{10}$-;

(c) —Z$^9$—C(O)—Z$^{10}$-;

(d) —Z$^9$—C(S)—Z$^{10}$-;

(e) —Z$^9$—O—Z$^{10}$-;

(f) —Z$^9$—S—Z$^{10}$-;

(g) —Z$^9$—O—C(O)—Z$^{10}$-; or (h) —Z$^9$—C(O)—O—Z$^{10}$-;

Z$^6$ is alkyl, alkenyl, alkynyl, cycloalkyl, cycloalkylalkyl, cycloalkenyl, cycloalkenylalkyl, aryl or aralkyl;

Z$^7$ and Z$^8$ are each independently hydrogen, alkyl, cycloalkyl, cycloalkylalkyl, cycloalkenyl-alkyl, aryl or aralkyl, or Z$^7$ and Z$^8$ together are alkylene or alkenylene, completing a 3- to 8-membered saturated or unsaturated ring together with the nitrogen atom to which they are attached;

Z$^9$ and Z$^{10}$ are each independently a single bond, alkylene, alkenylene or alkynylene;

Z$^{11}$ is (a) hydrogen; or (b) alkyl, cycloalkyl, cycloalkylalkyl, cycloalkenylalkyl, aryl or aralkyl;

or any two of Z$^7$, Z$^8$ and Z$^{11}$ together are alkylene or alkenylene, completing a 3- to 8-membered saturated or unsaturated ring together with the atoms to which they are attached;

each m is independently 1 or 2; and each n is independently 0, or 2.

For compound I, it is preferred that:

R$^2$ and R$^3$ are each independently hydrogen or alkyl;

R$^4$ and R$^5$ are each independently alkyl; and

R$^{12}$ and R$^{13}$, together with the nitrogen atom to which they are attached, form

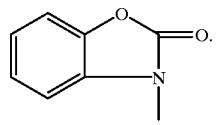

Most preferred compounds are those wherein:

R$^2$ and R$^3$ are each hydrogen; and

R$^4$ and R$^5$ are each alkyl of 1 to 4 carbon atoms, especially methyl.

DETAILED DESCRIPTION OF THE INVENTION

Listed below are definitions of terms used in this specification. These definitions apply to the terms as used throughout this specification, individually or as part of another group, unless otherwise limited in specific instances.

The term "alkyl" or "alk-" refers to straight or branched chain hydrocarbon groups having 1 to 10 carbon atoms, preferably 1 to 7 carbon atoms. The expression "lower alkyl" refers to alkyl groups of 1 to 4 carbon atoms.

The term "alkoxy" refers to alkyl-o-. The expression "lower alkoxy" refers to lower alkyl-o-.

The term "aryl" or "ar-" refers to phenyl, naphthyl and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —(CH$_2$)$_x$- wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH═CH—CH═CH-, —CH$_2$—CH═CH-, —CH$_2$-CH═CH-CH$_2$—, —C(CH$_3$)$_2$CH═CH— and —CH(C$_2$H$_5$)—CH═CH.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are -C≡C-, —CH$_2$-C≡C—, —CH(CH$_3$)—C≡C— and —C≡C-CH(C$_2$H$_5$)CH$_2$—.

The term "alkanoyl" refers to groups of the formula C(O)alkyl.

The terms "cycloalkyl" and "cycloalkenyl" refer to cyclic hydrocarbon groups of 3 to 8 carbon atoms.

The term "hydroxyalkyl" refers to an alkyl group including one or more hydroxy radicals such as —CH$_2$CH$_{20}$H, —CH$_2$CH$_2$OHCH$_2$OH, -CH(CH$_2$OH)$_2$ and the like.

The terms "halogen" and "halo" refer to fluorine, chlorine, bromine and iodine.

Throughout the specification, groups and substituents thereof are chosen to provide stable moieties and compounds.

The compounds of formula I form salts which are also within the scope of this invention. Pharmaceutically acceptable (i.e., non-toxic, physiologically acceptable) salts are preferred, although other salts are also useful, e.g, in isolating or purifying the compounds of this invention.

The compounds of formula I may form salts with alkali metals such as sodium, potassium and lithium, with alkaline earth metals such as calcium and magnesium, with organic bases such as dicyclohexylamine, benzathine, N-methyl-D-glucamide and hydrabamine, and with amino acids such as arginine, lysine and the like. Such salts may be obtained by reacting compound I with the desired ion in a medium in which the salt precipitates or in an aqueous medium followed by lyophilization.

When the $R^1$ to $R^5$ substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate, and various other sulfonates, nitrates, phosphates, borates, acetates, tartrates, maleates, citrates, succinates, benzoates, ascorbates, salicylates and the like. Such salts may be formed by reacting compound I in an equivalent amount of the acid in a medium in which the salt precipitates or in an aqueous medium followed by lyophilization.

In addition, when the $R^1$ to $R^5$ substituents comprise a basic moiety such as amino, zwitterions ("inner salts") may be formed.

Certain of the $R^1$ to $R^5$ substituents of compound I may contain asymmetric carbon atoms. Such compounds of formula I may exist, therefore, in enantiomeric and diastereomeric forms and in racemic mixtures thereof. All are within the scope of this invention. Additionally, compound I may exist as enantiomers even in the absence of asymmetric carbons. All such enantiomers are within the scope of this invention.

The compounds of formula I are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; anti-fibrillatory agents; anti-asthmatic agents; anti-atherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulin-dependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, osteoarthritis, sarcoidosis and eczematous dermatitis (all types of dermatitis).

The compounds of this invention can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; dual NEP-ACE inhibitiors; HMG CoA reductase inhibitors such as pravastatin and mevacor; squalene synthetase inhibitors; bile acid sequestrants such as questran; calcium channel blockers potassium channel activators beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologiclly acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The compounds of the present invention may be prepared as follows.

Scheme 1

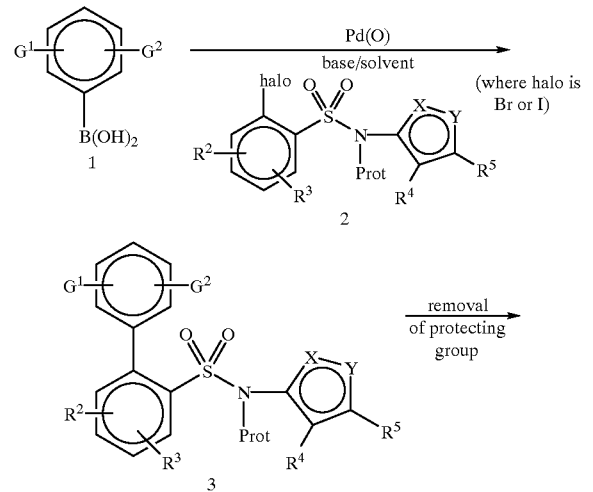

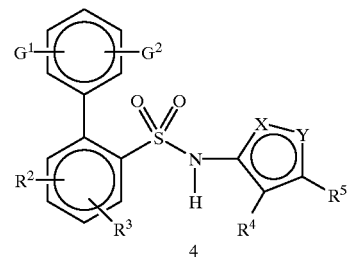

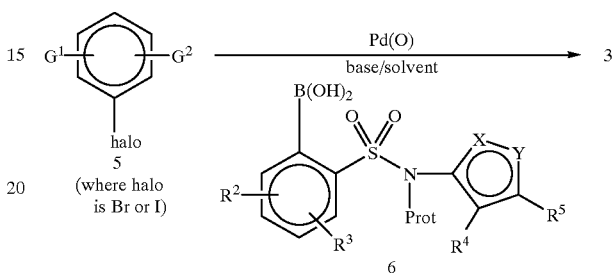

As depicted in Scheme 1, a suitably substituted aryl boronic acid 1 may be coupled with a 2-halo-phenylsulfonamide 2 under Pd(O) catalysis, in the presence of a base, such as aqueous sodium carbonate, and solvent, such as a mixture of toluene and ethanol, to give after deprotection, the title compounds 4. (The 2-halo phenylsulfonamide 2 may be prepared by the methods described in EP Publication Number 0,569,193 (1993)).

Alternatively, a suitably substituted aryl halide 5, either commercially available or prepared by methods known in the art, may be coupled with a phenylsulfonamide-2-boronic acid 6, under Pd(O) catalyzed conditions analogous to those described above, to give the products 3. These products are deprotected to give the title compounds 4.

A boronic acid intermediate 6 may be prepared from a 2-halo-phenylsulfonamide 2 by lithiation with a suitable alkyl lithium (such as n-butyl lithium), subsequent treatment with a trialkylborate (e.g., triisopropyl borate) and finally adding an aqueous acid such as aqueous hydrochloric acid.

Scheme 2

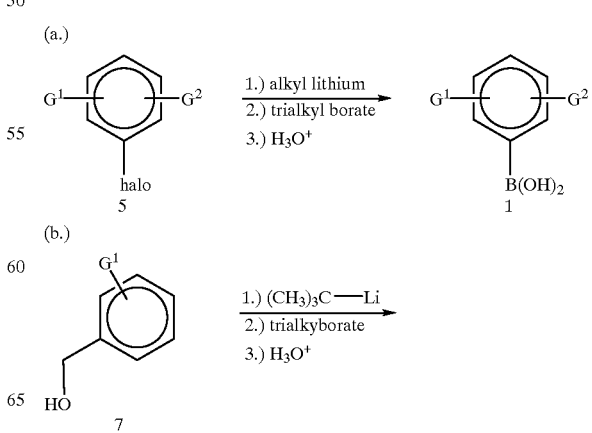

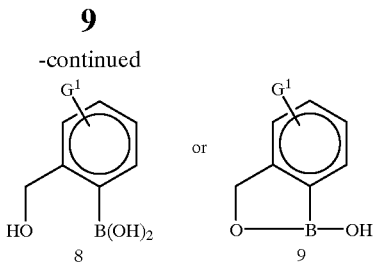

The subsituted aryl boronic acid 1 may be prepared from 5 as shown in Scheme 2(a). Treatment of 5 with an alkyl lithium reagent, such as n-butyl-, s-butyl- or t-butyl lithium, followed by reaction of the intermediate aryl lithium with a trialkylborate, such as trimethylborate, and then hydrolysis, gives the aryl boronic acid 1.

In the case where $G^2 = CH_2OH$, 1 may also be prepared as shown in Scheme 2(b) by treatment of compound 7 with an alkyl lithium reagent, such as t-butyl lithium, in the presence of a chelating agent, such as tetramethylethylenediamine (TMEDA), followed by reaction of the intermediate aryl lithium with a trialkylborate and hydrolysis to give the arylboronic acid 8, which may also exist as the arylboronic acid 9.

straight-chained lower alkyl, substituted arylhalide 10 may also be first converted into a boronic acid 11, as described in Scheme 2(a), and then reacted with the aryl halide 2 under Pd(O)—catalyzed conditions as described in Scheme 1. The resulting biarylsulfonamide 12 may then be converted to 3 by methods known in the art and deprotected to give the title compounds 4.

In each case, the boronic acid group of compound 1, 6, 8, 9 or 11 may be replaced by a trialkyltin moiety, -SnR", where R" is lower alkyl, and the halo group of compound 2, 5 or 10 may be replaced by a $—OS_{O2}CF_3$ moiety in the Pd-catalyzed coupling reaction. For general strategies in biaryl synthesis, see: Bringmann et al., *Angew. Chem. Int., Ed. Engl.* 29(1990) 977–991.

For compounds wherein any of $R^1$ to $R^5$ comprise reactive functionalities, the reactants may be treated with protecting agents prior to coupling. The amine portion of the sulfonamide core may also need to be protected when different $R^1$, $R^2$ and $R^3$ groups are added. Suitable protecting agents and procedures for use thereof are generally known in the art. Exemplary protecting groups are benzyl, halocarbobenzyloxy, tosyl, methyl and the like for hydroxyl; and carbobenzyloxy, halocarbobenzyloxy, t-butoxy carbonyl, acetyl, benzoyl, methoxyethoxymethyl and the

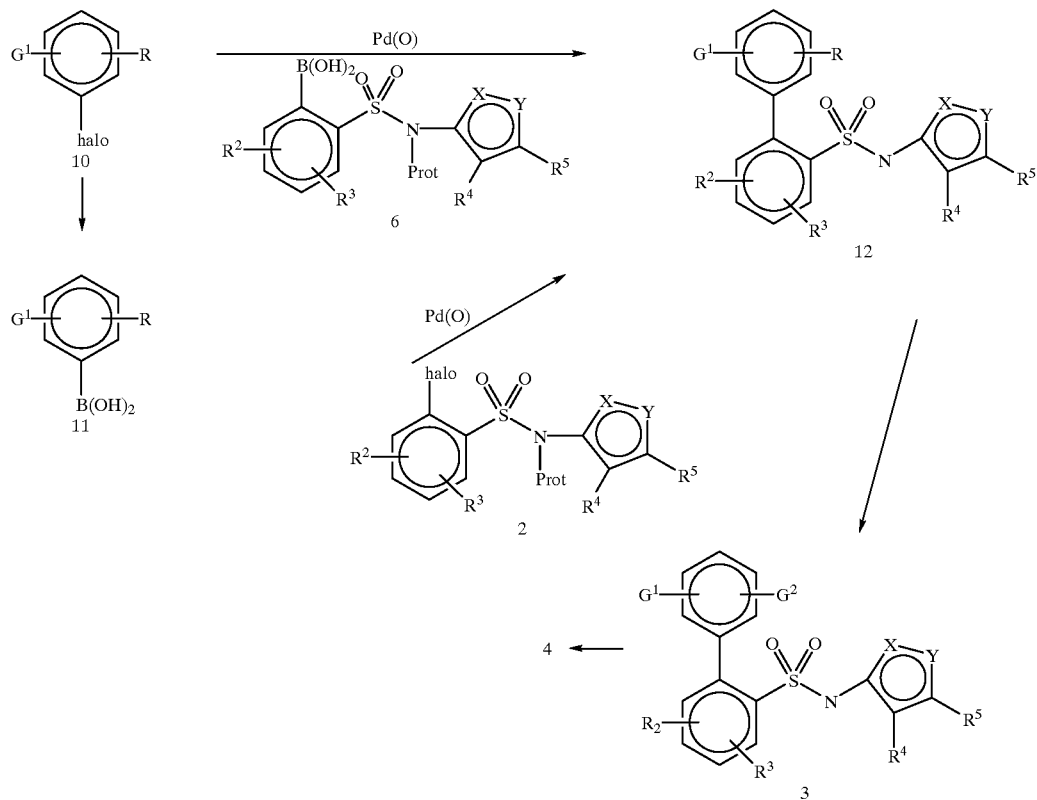

Scheme 3

As depicted in Scheme 3, the $G^2$ group may also be introduced after formation of the biaryl sulfonamide by a Pd(O)-catalyzed coupling reaction. Specifically, a substituted arylhalide 10, commercially available or prepared by methods known in the art, where R is a straight-chained lower alkyl or —C(O)—R' (where R' is H or lower alkoxy), may be reacted with the arylboronic acid 6 under Pd(O)-catalyzed conditions as described in Scheme 1. When R is a like for amino. The sulfonamide nitrogen may be protected with methoxyethoxymethyl, trimethylsilylethoxymethyl, t-butyl and the like. Protecting groups may be removed from the resulting protected analogues of compound I by treatment with one or more deprotecting agents. Suitable deprotecting agents and procedures for use thereof are generally known in the art.

The invention will now be further described by the following working examples, which are preferred embodiments of the invention. These examples are meant to be illustrative rather than limiting.

EXAMPLE 1

N-(3,4-Dimethyl-5-isoxazolyl)-2'-(hydroxymethyl) [1,1'-biphenyl]-2-sulfonamide

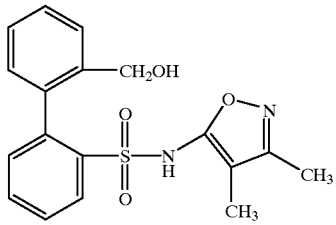

A. 1,3-Dihydro-l-hydroxy-2,1-benzoxaborole

To a solution of 2-bromobenzyl alcohol (2.8 g, 15 mmol) in 30 ml of tetrahydrofuran (THF) under argon at -40° C., a 2.0 M solution of butyllithium in hexanes (15.5 ml) was added dropwise over 15 minutes. The solution was stirred for an additional 15 minutes and trimethylborate (3.22 g, 31.0 mmol) was added. After 15 minutes at -40° C., the solution was warmed to room temperature and stirred for a further 2 hours. The reaction was quenched by the addition of 10% aqueous hydrochloric acid (HCl) (100 ml), and after 10 minutes, the solution was extracted with ethyl acetate (3×75 ml). The combined ether extracts were then extracted with 2N aqueous sodium hydroxide (NaOH) (3×50 ml). The aqueous extracts were then acidified with dilute hydrochloric acid to pH 2 and extracted with 3×50 ml of ethyl acetate. The combined organic extracts were washed once with water (100 ml), dried and evaporated to afford 0.43 g (21%) of compound A as a white solid (m.p. 138–140° C.).

B. N-(3,4-Dimethyl-5-isoxazolyl)-2-bromo-benzenesulfonamide

To a solution of 3.0 g (11.74 mmol) of 2-bromobenzenesulfonyl chloride in 10 ml of pyridine was added 1.32 g (11.74 mmol) of 3,4-dimethyl-5-isoxazolamine. The mixture was stirred at room temperature under argon overnight, added to 150 ml of ice water and filtered. The filtrate was acidified to pH 2 using 6N aqueous hydrochloric acid and the grey solid was filtered and dried. The solid was crystallized from methanol/water to afford 4.0 g (>100%) of compound B as tan crystalline needles (m.p. 125–126° C.).

C. 2-Bromo-N-(3,4-dimethyl-5-isoxazolyl)-N-(methoxyethoxymethyl) benzenesulfonamide To a solution of 1.1 g (3.33 mmol) of compound B in 15 ml of THF at room temperature under argon was added 0.19 g (4.8 mmol) of sodium hydride (60% suspension in mineral oil) in portions, and the solution was stirred at room temperature for 10 minutes. Methoxyethoxymethyl chloride (0.55 g, 4.4 mmol) was then added and the solution was stirred overnight. The mixture was concentrated and diluted with 30 ml of water, and extracted with 40 ml of ethyl acetate. The combined organic extracts were washed with 50 ml of brine, dried and evaporated to provide 1.2 g (87%) of compound C as a brown gum.

D. N-(3,4-Dimethyl-5-isoxazolyl)-2'-(hydroxymethyl)-N-[(2-methoxyethoxy) methyl][1,1'-biphenyl]-2-sulfonamide To a solution of 1.02 g (2.43 mmol) of compound C and 0.14 g (0.12 mmol) of tetrakis-(triphenylphosphine) palladium(O) in 30 ml of toluene under argon, 18 ml of 2M aqueous sodium carbonate was added. 0.36 g (2.67 mmol) of compound A was then added in 25 ml of 95% ethanol. The mixture was refluxed for 4 hours, diluted with 100 ml of water, and extracted with 3×50 ml of ethyl acetate. The combined organic extracts were washed once with 100 ml of brine, dried and evaporated. The residue was chromatographed on 50 g of silica gel using 2% methanol in dichloromethane to afford 0.93 g (86%) of compound D as a light brown gum which solidified on standing. $R_f$=0.11 (Hexanes:ethyl acetate 2:1).

E. N-(3,4-Dimethyl-5-isoxazolyl)-2'-(hydroxymethyl) [1,1'-biphenyl]-2-sulfonamide To a solution of 0.10 g (0.224 mmol) of compound D in 3 ml of 95% ethanol, 3 ml of 6N aqueous HCl was added and refluxed for 1.5 hours. The mixture was concentrated and diluted with 20 ml of water. The mixture was then extracted with 3×20 ml of ethyl acetate and the combined organic extracts were washed once with 50 ml of brine, dried and evaporated to provide a brown foam. The residue was chromatographed on 10 g of silica gel using 2% methanol in dichloromethane to afford 0.03 g (37%) of the title compound as a white foam (m.p. 70–80° C. (amorphous)).

Analysis calculated for $C_{22}H_{26}N_2O_4S$ $0.26H_2O$: C, 59.55; H, 5.14; N, 7.72; S, 8.83. Found: C, 59.55; H, 5.18; N, 7.72; S, 8.43.

EXAMPLE 2

4'-[(2,3-Dihydro-2-oxo-3-benzoxazolylmethyl]-N-(3,4-dimethyl-5-isoxazolyl) [1,1'-biphenyl]-2-sulfonamide

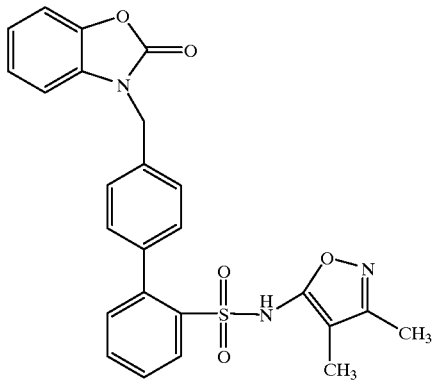

A. N-(3.4-Dimethyl-5-isoxazolyl)-N-[(2-methoxyethoxy) methyl]-4'-methyl[1,1'-biphenyl]-2-sulfonamide To a solution of compound C from Example 1, 4-methylbenzeneboronic acid (4.76 g, 35 mmol) in 250 ml of toluene and 200 ml of 95% ethanol under argon, tetrakis (triphenylphosphine)palladium(0) (2.43 g, 2.1 mmol) was added, followed by 150 ml of 2M aqueous sodium carbonate. The reaction mixture was heated at 80° C. for 2.5 hours, cooled and diluted with 300 ml of ethyl acetate. The organic liquid was separated and washed with 200 ml water and 200 ml of brine, dried and concentrated. The residue was chromatographed on silica gel using 5:1 hexane/ethyl acetate to afford compound A (9.0 g, 60%) as a colorless gum. $R_f$=0.74, silica gel, 1:1 Hexane/ethyl acetate.

B. 4'-(Bromomethyl)-N-(3,4-dimethyl-5-isoxazly) -N-[(2-methoxyethoxy)mnethyl][1,1'-biphanyl]-2-sulfonamide To compound A (7.7 g, 17.89 mmol) in 180 ml carbon tetrachloride, n-bromosuccinimide (4.14 g, 23.25 mmol) and benzoyl peroxide (385 mg, 1.59 mmol) were added. The reaction was refluxed for 1.5 hours. After cooling, the reaction mixture was diluted with 200 ml dichloromethane, washed with 2×100 ml water and 100 ml brine, dried and concentrated. The residue was chromatographed on silica gel eluting with 4:1 hexane/ethyl acetate to provide compound B (3.64 g, 40%) as a colorless gum. $R_f$=0.38, silica gel, 2:1 Hexane/ethyl acetate.

C. 4'-[(2,3-Dihydro-2-oxo-3-benzoxazolyl) methyl]-N-(3,4-dimethyl-5-isoxazolyl)-N-[(2-methoxyethoxy) methyl][(1,1-biphenyl]-2-sulfonamide To compound B (200 mg, 0.39 mmol) and 2-benzoxazolinone (58 mg, 0.43 mmol) in 0.79 ml dimethylformamide (DMF), $K_2CO_3$ (109 mg, 0.79 mmol) was added. The reaction was stirred at room temperature for 4 hours and then at 45° C. for 0.5 hours. The mixture was diluted with 30 ml ethyl acetate, washed with 2×10 ml water and 10 ml brine, dried and concentrated. The residue was chromatographed on silica gel using 2.5:1 hexane/ethyl acetate to afford compound A (170 mg, 77%) as a colorless gum. $R_f$=0.32, silica gel, 1:1 hexane/ethyl acetate.

D. 4'-[(2,3-Dihydro-2-oxo-3-benzoxazolyl) methyl]-N-(3,4-dimethyl-5-isoxazolyl) [1,1'-biphenyl]-2-sulfonamide To a solution of compound A (170 mg, 0.30 mmol) in 4 ml of 95% ethanol, 4 ml of 6 N aqueous HCl was added. The reaction was refluxed for two hours, cooled and concentrated. The residue was diluted with 25 ml of ethyl acetate, washed with 2×10 ml water and 10 ml of brine, dried and concentrated to provide a white solid (140 mg, 97%), which was crystalized from dichloromethane/hexane to give the title compound as white crystals (m.p. 182–183° C.). Analysis calcualted for $C_{25}H_{21}N_3O_5S$* 0.58 $H_{2O}$ Calculated: C, 61.78; H, 4.60; N, 8.65; S, 6.60. Found: C, 61.84; H, 4.33; N, 8.59; S, 6.55.

EXAMPLE 3

4'[(Dimethylamino)methyl]-N-(3,4-dimethyl-5-isoxazolyl) [1,1'-biphenyl]-2-sulfonamide, hydrochloride

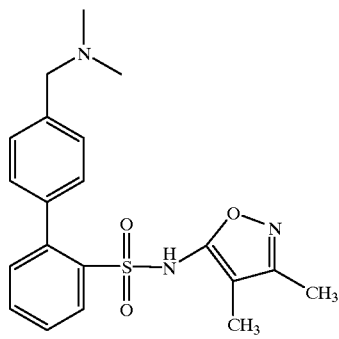

A. 4'-[(Dimethylamino)methyl1]-N-(3,4-dimethyl-5-isoxazolyl) -N-[(2-methoxyethoxy)methyl][1,1'-biphenyl]-2-sulfonamide, hydrochloride To compound B from Example 2 (200 mg, 0.39 mmol) in 1 ml methanol, 1.6 ml 40% aqueous dimethylamine was added. The reaction was stirred at room temperature overnight and concentrated. The mixture was diluted with 30 ml ethyl acetate, washed with 10 ml water and 10 ml brine, dried and concentrated. The residue was chromatographed on silica gel using ethyl acetate to afford compound A (145 mg, 78%) as a colorless gum. $R_f$=0.34, silica gel, 10:1 dichloro-methane/methanol.

B. 4'-[(Dimethylamino)methyl]-N-(3,4-dimethyl-5-isoxazolyl) [1,1'-biphenyl]-2-sulfonamide, hydrochloride To a solution of compound A (145 mg, 0.31 mmol) in 4 ml of 95% ethanol, 4 ml of 6 N aqueous HCl was added. The reaction was refluxed for 2 hours, cooled and concentrated. The mixture was neutralized with saturated aqueous $NaHCO_3$, and then acidified to pH-5 with acetic acid. The solution was extracted with 3×20 ml dichloromethane, and the combined organic extracts were washed with 10 ml brine, dried and concentrated to give a colorless gum (115 mg, 97%), which was dissolved in 1 N HCl and concentrated under vacuum to provide the hydrochloride salt of the title compound as a white solid (m.p. 126–130° C.). Analysis calcualted for $C_{20}H_{24}N_3ClO_3S$* 1.2 $H_2O$ Calculated: C, 54.16; H, 6.00; N, 9.47; S, 7.23; Cl, 7.99. Found: C, 54.22; H, 6.00; N, 9.39; S, 7.02; Cl 8.39.

EXAMPLE 4

N-(3,4-Dimethyl-5-isoxazolyl)-4'-[(2-hydroxyethoxy) methyl][1,1'-biphenyl]-2-sulfonamide

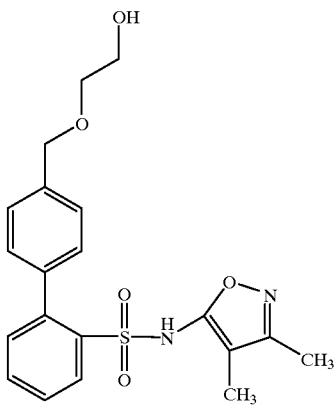

A. N-(3,4-Dimethyl-5-isoxazolyl)-4 1'-[(2-hydroxyethoxy) methyl]-N-[(2-methoxyethoxy) methyl][1,1'-biphenyl]-2-sulfonamide To ethylene glycol (98 mg, 1.57 mmol) in 0.5 ml THF and 0.5 ml DMF at 0° C., sodium hydride (NaH) (60% in mineral oil, 31 mg, 0.79 mmol) was added. The mixture was stirred at room temperature for 20 minutes and a solution of compound B from Example 2 (200 mg, 0.39 mmol) in 1.5 ml THF was added. The reaction mixture was heated at 45° C. overnight. Additional ethylene glycol (98 mg, 1.57 mmol) and NaH (60% in mineral oil, 31 mg, 0.79 mmol) were added and the mixture was heated at 50° C. for another 4 hours. The mixture was then added to 15 ml saturated aqueous ammonium chloride ($NH_4Cl$) and extracted with 3×20 ml ethyl acetate. The combined organic extracts were washed with 10 ml water and 10 ml of brine, dried and concentrated. The residue was chromatographed on silica gel using 2:3 hexane/ethyl acetate to afford compound A (103 mg, 53%) as a colorless gum. $R_f$=0.15, silica gel, 1:2 hexane/ethyl acetate.

B. N-(3,4-Dimethyl-5-isoxazolyl)-4'-[(2-hydroxyethoxy) methyl][1,1'-biphenyl]-2-sulfonamide To a solution of compound A (102 mg, 0.21 mmol) in 2.8 ml of 95% ethanol, 2.8 ml of 6 N aqueous HCl was added.

The reaction was refluxed for 1 hour and 45 minutes, cooled and concentrated. The mixture was neutralized with saturated aqueous NaHCO$_3$, and then acidified to pH-5 with acetic acid. The mixture was extracted with 3×20 ml ethyl acetate and the combined organic extracts were washed with 10 ml brine, dried and concentrated. The residue was chromatographed on silica gel using 100:2 dichloromethane/methanol to afford the title compound (58 mg, 69%) as a colorless gum. Analysis calcualted for C$_{20}$H$_{22}$N$_2$O$_5$S. 0.14 H$_2$O Calculated: C, 59.31; H, 5.55; N, 6.92; S, 7.92. Found: C, 59.14; H, 5.36; N, 7.09; S, 8.18.

EXAMPLE 5

N-(3,4-Dimethyl-5-isoxazolyl)-2'-(hydroxymethyl)-4'-(2-methylpropyl)[1,'-biphenyl]-2-sulfonamide

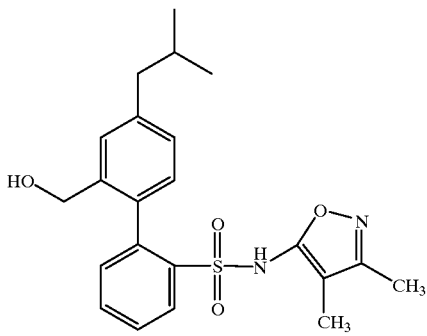

A. 3-(2-Methylpropyl)benzenemethanol

To a solution of isobutylene (4.40 g, 78.45 mmol) in 11 ml THF at -78° C., 9-Bora-bicyclo[3.3.]nonane (9-BBN) (0.5 M in THF, 157 ml, 78.45 mmol) was added. The mixture was stirred at -78° C. for 3 hours, and then warmed to room temperature and stirred overnight to form 9-(2-Methylpropyl) -9-borabicyclo[3.3.1]nonane (-9-isobutyl BBN). In a separate flask, to a solution of 3-bromobenzylalcohol (13.34 g, 71.32 mmol) in 36 ml THF, tetrakis(triphenylphosphine)palladium(0) (2.47 g, 2.14 mmol) and 60 ml 3M NaOH were added. The 9-isobutyl BBN prepared above was then transferred into the flask under argon and the mixture was refluxed for 21 hours. The mixture was cooled with an external ice bath and 18 ml 30% hydrogen peroxide was added. The mixture was stirred for 30 minutes, concentrated to about 100 ml and partitioned between 200 ml each of water and ethyl acetate. The aqueous layer was extracted with ethyl acetate (2×100 ml) and the combined organic extracts were washed with 60 ml brine, dried and concentrated. The residue was chromatographed on silica gel using 9:1 hexane/ethyl acetate to afford compound A (8.16 g, 70%) as a liquid.

B. 1,3-Dihydro-1-hydroxy-5-(2-methylpropl) -2,1-benzoxaborole

To a solution of compound A (1.00 g, 6.09 mmol) and N,N,N',N'-Tetramethylethylenediamine (TMEDA) (2.48 g, 21.31 mmol) in 12 ml ethyl ether under argon at -78° C., t-butyl lithium (1.7 M in pentane, 12.5 ml, 21.31 mmol) was added over 5 minutes. The mixture was warmed to room temperature, stirred for 4 hours, and cooled to -40° C. Trimethylborate (2.21 g, 21.31 mmol) was added in one portion. The solution was warmed to room temperature, stirred for 1.5 hours and cooled to 0° C., and 15% aqueous HCl (40 ml) was added. The solution was extracted with 3×20 ml ethyl acetate and the combined aqueous extracts were extracted with 6×25 ml 2N NaOH. The combined aqueous extracts were acidified to pH 2 with 6 N aqueous HCl and the solution was extracted with 3×50 ml ethyl acetate. The combined organic extracts were washed once with 40 ml brine, dried and concentrated to afford compound B as a light yellow solid (384 mg, 33%) (m.p. 96–100° C.). R$_f$=0.4, silica gel, 3:1 hexane/ethyl acetate.

C. N-(3,4-dimethyl-5-isoxazolyl)-21'-(hydroxymethyl)-N-[(2-methoxyethoxy)methyl]-4'-(2-methylpropyl) [1,1'-biphenyl]-2-sulfonamide To a solution of compound C from Example 1 (784 mg, 1.87 mmol) and tetrakis(triphenyl-phosphine) palladium(O) (130 mg, 0.112 mmol) in 14 ml of toluene under argon, 8.0 ml of aqueous sodium carbonate was added followed by compound B (356 mg, 1.87 mmol) in 11 ml of 95% ethanol. The reaction mixture was heated at 80° C. for 4 hours, cooled and diluted with 40 ml of ethyl acetate. The organic layer was separated and washed with 2×20 ml of brine, dried and concentrated. The residue was chromatographed on silica gel using 2.5:1 hexane/ethyl acetate to afford compound C (550 mg, 58%) as a colorless gum. R$_f$=0.18, silica gel, 2:1 hexane/ethyl acetate.

D. N-(3,4-dimethyl-5-isoxazolyl)-2'-(hydroxymethyl) -4'-(2-methylpropyl) [1,1'-biphenyl]-2-sulfonamide To a solution of compound C (120 mg, 0.24 mmol) in 8 ml of 95% ethanol, 8 ml of 6 N aqueous HCl was added and refluxed for 2 hours. The reaction mixture was concentrated to about 8 ml and extracted with 3×15 ml of ethyl acetate. The organic extracts were washed with 10 ml of brine, dried and concentrated. The residue was purified by preparative HPLC on a 30×500 mm column using 72% solvent A (90% methanol, 10% water, 0.1% TFA) and 28% solvent B (10% methanol, 90% water, 0.1% TFA) to provide the title compound (50 mg, 50%) as a white solid (m.p. 60–67° C. (amorphous)).

Analysis calcualted for C$_{22}$H$_{26}$N$_2$O$_4$S. 0.18 H$_2$O Calculated: C, 63.26; H, 6.36; N, 6.71; S, 7.68. Found: C, 63.39; H, 6.18; N, 6.58; S, 7.90.

EXAMPLE 6

2'-(Aminomethyl)-N-(3,4-dimethyl-5-isoxazolyl)-4'-(2-methylpropyl)[1,1'-biphenyl]-2-sulfonamide

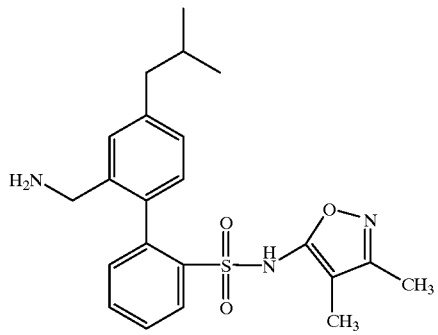

A. N-(3,4-Dimethyl-5-isoxazolyl)-2'-formyl-N-[(2-methoxyethoxy)methyl]-4'-(2-methylpropyl) [11,1'-biphenyl]-2-sulfonamide To oxalyl chloride (2M in dichloromethane, 9 mL, 18.0 mmol) in 26 mL dichloromethane at -78° C., a solution of DMSO (2.8 g, 35.8 mmol) in 39 mL dichloromethane was added and stirred for 10 minutes. Compound C from Example 5 (2.40 g, 4.78 mmol) in 39 mL of dichloromethane was then added and the reaction was stirred at -78° C. for 2 hours. Triethylamine (6.07 g, 60 mmol) was added and stirred at -78° C. for 5 minutes, and the reaction mixture was warmed to room temperature and stirred for 15 minutes. The reaction mixture was partitioned between 300 mL 0.5 N HCl and 200 mL dichloromethane, and the aqueous liquid was extracted with 150 mL dichloromethane. The combined organic extracts were dried and concentrated, and the residue was chromatographed on silica gel using 3.5:1 hexane/ethyl acetate to afford compound A (1.83 g, 77%).

B. N-(3,4-Dimethyl-5-isoxazolyl)-2'-formyl-4'-(2-methylproyl)[1,1'-biphenyl]-2-sulfonamide To a solution of compound A (617 mg, 1.23 mmol) in 30 mL of 95% ethanol, 30 mL of 6 N aqueous HCl was added and refluxed for 1.5 hours. The reaction mixture was concentrated to about 30 mL and extracted with 3×30 mL of ethyl acetate. The organic extracts were washed with 20 mL of brine, dried and concentrated. The residue was chromatographed on silic gel using 2.5:1 hexane/ethyl acetate to provide compound B (290 mg, 57%) as a white solid. M.p. 60–66° C. (amorphous).

C. 2'-(Aminomethyl)-N-(3,4-dimethyl-5-isoxazolyl) -4'-(2-methylpropyl) [1,1'-biphenyl]-2-sulfonamide A mixture of compound B (480 mg, 1.16 mmol), ammonium acetate (15.44 g, 232 mmol) and 3A molecular sieves (0.5 g) in 58 mL methanol was stirred at room temperature overnight. Sodium triacetoxyborohydride (740 mg, 3.49 mmol) was then added to the reaction mixture and stirred at room temperature for 1 hour. The solution was filtered, concentrated and partitioned between 150 mL methylene chloride and 25 mL water. The organic layer was separated, dried and concentrated. The residue was chromatographed on silica gel using 100:6 dichloromethane/methanol to provide the title compound (250 mg, 52%) as a white solid (m.p. >200° C. dec.). Analysis calculated for $C_{22}H_{27}N_3O_3S$* 0.26 $H_2O$ Calculated: C, 63.17; H, 6.63; N, 10.05; S, 7.66. Found: C, 63.09; H, 6.56; N, 10.13; S, 7.88.

EXAMPLE 7

N-(3,4-Dimethyl-5-isoxazolyl)-4'-(1-hydroxy-2-methylpropyl)[1,1'-biphenyl]-2-sulfonamide

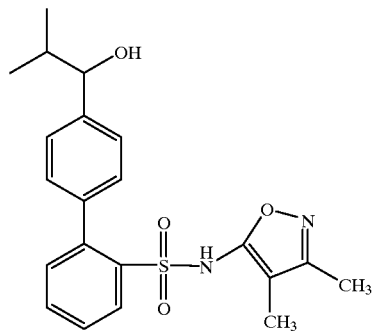

A. N-(3,4-Dimethyl-5-isoxazolyl)-4'-formyl-N-[(2-methoxyethoxy) methyl][1,1'-biphenyl]-2-sulfonamide To a solution of compound C from Example 1 (1.08 g, 2.58 mmol) and 0.15 g (0.129 mmol) of tetrakis (triphenylphosphine) palladium (0) in 25 ml of toluene under argon, 15 ml of 2 M aqueous sodium carbonate was added followed by 0.43 g (3.22 mmol) of 4-Formyl phenyl-boronic acid in 18 ml of 95% ethanol. The mixture was refluxed for 3 hours, diluted with 100 ml of water and extracted with 3×50 ml of ethyl acetate. The combined organic extracts were washed once with 100 ml of brine, dried and evaporated. The residue was chromatographed on 50 g of silica gel using hexanes/ethyl acetate 3:2 to afford 0.96 g (84%) of compound A as a colorless gum.

B. N-(3,4-Dimethyl-5-isoxazolyl)-4'-formyl [1,1'-biphenyl]-2-sulfonamide

To a solution of 0.30 g (0.675 mmol) of compound A in 10 ml of 95% ethanol, 10 ml of 6N aqueous HCl was added and refluxed for 2 hours. The mixture was concentrated and diluted with 50 ml of water. The mixture was then extracted with 3×50 ml of ethyl acetate and the combined organic extracts were washed once with 100 ml of brine, dried and evaporated to provide a white foam. The residue was chromatographed on 30 g of silica gel using 3% methanol in dichloromethane to afford 0.20 g (83%) of compound B as a colorless gum.

C. N-(3,4-Dimethyl-5-isoxazolyl)-4'-(1-hydroxy-2-methylpropyl) [1,1'-biphenyl]-2-sulfonamide To a solution of compound B (0.20 g, 0.56 mmol) in 25 ml of ether at 0C under argon, 0.62 ml of 2M isopropyl magnesium chloride in ether was added and stirred for 1 hour. The mixture was slowly warmed up to room temperature and stirred for an additional 3 hours. The mixture was then added to 50 ml of saturated aqueous potassium bisulfate and extracted with 3×50 ml of ethyl acetate. The combined organic extracts were washed once with 100 ml of brine, dried and evaporated. The residue was chromatographed on 20 g of silica gel using hexanes/ethyl acetate 3:2 containing 0.5% glacial acetic acid to afford 0.14 g of a colorless gum. This material was further purified by reverse phase preparative HPLC on a 30×500 mm column using 60% solvent A (90% methanol, 10% water, 0.1% TFA) and 40% solvent B (10% methanol, 90% water, 0.1% TFA) to provide 0.07 g (31%) of the title compound as a white foam (m.p. 60–70° C. (amorphous)). Analysis calculated for $C_{22}H_{26}N_2O_4S.0.27$ $H_2O$ Calculated: C, 62.24; H, 6.10; N, 6.91; S, 7.91. Found: C, 62.40; H, 6.01; N, 6.75; S, 8.10.

EXAMPLE 8

N-(3,4-Dimethyl-5-isoxazolyl)-4'-(2-hydroxy-2-methyl-propyl) [1,1'-biphenyl]-2-sulfonamide, monolithium salt

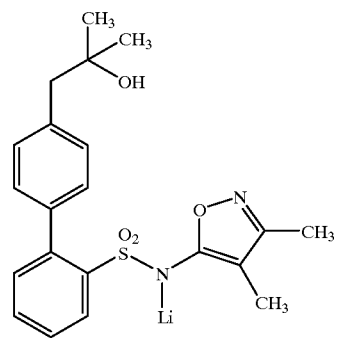

A. 4-Bromobenzeneacetic acid, methyl ester

A solution of 2.5 g (11.6 mmoles) of p-bromophenylacetic acid and 0.25 mL of concentrated sulfuric acid in 75 mL of methanol was heated at reflux for 2 hours.

After cooling, the solution was evaporated to dryness and the residue diluted with ethyl acetate. The solution was washed with saturated sodium bicarbonate (twice) and brine (twice), dried (MgSO$_4$), and the solvent removed to give a clear light orange oil.

Distillation (kugelrohr, 125° C., 0.1 mm) afforded 2.6 g (11.3 mmoles, 97 %) of compound A as a clear colorless oil.

B. 4-Bromo-α, α-dimethylbenzeneethanol

To 2.2 mL (6.6 mmoles) of 3 M methylmagnesium bromide in tetrahydrofuran (THF), with ice cooling and under argon, was added dropwise a solution of 0.5 g (2.2 mmoles) of compound A in 1 mL of THF. Stirring was continued with cooling for 1 hour, then at room temperature for 2 hours.

The reaction was added to ice-water with vigorous stirring and extracted with ether (three times). The combined ether layers were washed with brine (twice) and dried (MgSO$_4$), and the solvent removed to give 0.5 g of clear colorless oil. Distillation (kugelrohr, 125° C., 0.1 mm) yielded 0.4 g of oil which still contained an impurity by tlc (30% ethyl acetate-hexane).

This material was subjected to flash chromatography on a 75 cc column of silica gel. Elution with 20% ethyl acetate—hexane afforded 0.35 g (1.53 mmoles, 69 %) of compound B as a clear colorless oil.

C. 2-Borono-N-(3,4-dimethyl-5-isoxazolyl)-N-[(2-methoxyethoxy) methyl]benzenesulfonamide To a solution of compound C from Example 1 (5.67 g, 13.52 mmol) in 70 mL of tetrahydrofuran at -78° C., n-butyl lithium (2M solution in cyclohexane, 8.11 mL, 16.23 mmol) was added over 10 minutes. The resulting solution was stirred at -78° C. for 15 minutes and triisopropylborate (1.52 g, 8.06 mmol) was added. The mixture was then warmed to room temperature and stirred for 2 hours. The mixture was cooled to 0° C., 10% aqueous hydrochloric acid (120 ml) was added, and the solution was stirred for 10 minutes. The mixture was concentrated to 120 mL and extracted with 4×60 mL ethyl acetate. The combined organic extracts were washed once with 100 mL brine, dried (MgSO$_4$) and concentrated to give compound B (4.25 g, 82%) as a light yellow gum.

D. N-(3,4-Dimethyl-5-isoxazolyl)-4'-(2-hydroxy-2-methylpropyl) -N-[(2-methoxyethoxy)methyl]-[1,1'-biphenyl]-2-sulfonamide To a degassed solution of 324 mg (1.4 mmole) of compound B and 506 mg (1.4 mmoles) of compound C in 5 mL of toluene, 4 mL of 95% ethanol and 3.5 mL of 2 M sodium bicarbonate, at room temperature and under argon, was added 116 mg (0.1 mmole) of tetrakis(triphenylphosphine)palladium(0), and the reaction was heated at 80° C. for 3 hours.

After cooling to room temperature, the reaction was diluted with ethyl acetate, washed with brine (three times) and dried (MgSO$_4$), and the solvent was removed to give a clear orange oil.

This material was subjected to flash chromatography on a 75 cc column of silica gel. Elution with 50% ethyl acetate—hexane, followed by 75% ethyl acetate - hexane afforded 189 mg (0.38 mmole, 28%) of compound D as a viscous oil.

E. N-(3,4-Dimethyl-5-isoxazolyl)-4'-(2-hydroxy-2-methyl-propyl) [1,1'-biphenyl]-2- sulfonamide, mono-lithium salt A solution of 180 mg (0.37 mmole) of compound D in 4 mL of ethanol and 4 mL of 6 N HCl was heated at reflux for 5 hours. Even though starting material still appeared to be present by tlc, the reaction was worked up.

The reaction was evaporated to near dryness. The residue was rendered alkaline with saturated sodium bicarbonate and extracted with ethyl acetate (three times). The combined extracts were washed with brine and dried (MgSO$_4$), and the solvent was removed to yield unreacted compound D as an orange oil. The combined aqueous layers were acidified with 6 N HCl and extracted with ethyl acetate (three times). The combined extracts were washed with brine and dried (MgSO$_4$), and the solvent was removed to yield 18 mg of the title compound as a viscous oil.

The recovered compound D was taken into 1 mL of ethanol and 1 mL of 6 N HCl and heated at reflux for an additional 5 hours. Starting material still appeared to be present by tlc but the reaction was not heated further.

The reaction was evaporated to complete dryness and the residue subjected to flash chromatography on a 35 cc column of silica gel. Elution with a step-wise gradient from 1 to 5 % methanol—chloroform afforded 41 mg of the desired title compound.

The two portions of product were combined and resubjected to flash chromatography on a 35 cc column of silica gel. Elution with 5% methanol—trichloromethane gave 44 mg of compound D of insufficient purity. This material was then subjected to prep. HPLC on a YMC S5 120A ODS column. Elution with a linear gradient of 50–100% methanol—H$_2$O (+0.1% TFA) afforded 29 mg of the title compound as a white glass.

This material was taken into methanol and 10 mg of lithium hydroxide. H$_2$O was added and the mixture stirred until solution was obtained. The solvent was removed and the residue chromatographed on a 20 cc column of HP-20 resin. After initial elution with 100% water and 10% methanol—water, continued elution with 50% methanol—water afforded 11 mg (0.027 mmole, 7%) of the title compounds as a white powder. M.p.: 170–172° C. (dried: 50° C., high vac, overnight). MS: (M+Li)$^+$407$^+$Calculated for C$_{21}$ H$_{23}$ N$_2$O$_4$S Li. 1.65 H$_2$O: C, 57.84; H, 6.08; N, 6.42. Found: C, 58.04; H, 6.19; N, 6.22.

EXAMPLE 9

N-(3,4-Dimethyl-5-isoxazolyl)-4'-(3-hydroxy-2-methylpropyl) [1,1'-biphenyl]-2-sulfonamide, lithium salt

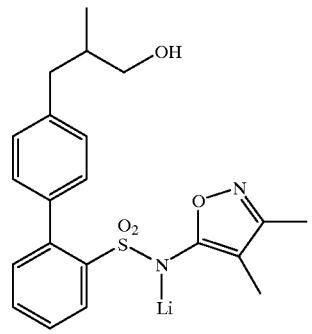

A. 4-Bromo-α-methylbenzenpropanoic acid, ethyl ester

A solution of lithium diisopropyl amide (LDA) was prepared at -78° C. under argon, by the addition of 19.2 mL (48 mmoles) of 2.5 M n-butyl lithium to a solution of 7 mL (50 mmoles) of diisopropylamine in 11 mL of dry tetrahydrofuran (THF).

To the LDA solution at -78° C., was added dropwise a solution of 5 mL (44 mmoles) of ethyl propionate in 20 mL of THF. Stirring was continued at —78° C. for 1 hour, after which a solution of 10 g (40 mmoles) of p-bromo benzylbromide in 25 mL of THF was added dropwise. Stirring was continued at -78° C. for 2 hours. Water was then added dropwise and the reaction was allowed to warm to room temperature.

The solution was evaporated to near dryness and the residue diluted with ethyl acetate. The solution was washed with brine, saturated sodium bicarbonate and brine (twice), and dried (MgSO$_4$), and the solvent was removed to give a clear, pale yellow oil.

This material was subjected to flash chromatography on a 500 cc column of silica gel. Elution with 25% dichloromethane—hexane afforded 4.1 g (approx 30%) of a cloudy oil which was used without further purification.

B. 4-Bromo-β-methylbenzenepropanol

To a solution of 4.0 g (assumed 14.7 mmoles) of compound A in 75 mL of toluene, at -78° C. and under argon, was added dropwise 37 mL (37 mmoles) of 1 M diisobutyl aluminum hydride (DIBAL) in toluene. Stirring was continued at -78° C. for 3 hours. To the cold reaction was then added 5.5 mL of methanol, followed by 7.4 mL of water, and the reaction was allowed to warm to room temperature. Stirring was continued for an additional 1 hour. The resulting white precipitate was removed by filtration and the filter cake washed well with ethyl acetate.

The clear colorless filtrate was evaporated to dryness to yield an oil residue which was subjected to flash chromatography on a 500 cc column of silica gel. Elution with 25% ethyl acetate—hexane afforded 2.0 g (59%) of pure compound B as a clear colorless oil.

C. N-(3,4-Dimethyl-5-isoxazolyl)-4'-(3-hydroxy-2-methylpronyl) -N-[(2-methoxyethoxy)methyl]-[1,1'-biphenyl]-2-sulfonamide To a degassed solution of 230 mg (1 mmole) of compound B and 460 mg (1.2 mmoles) of compound C from Example 8 in 5 mL of toluene, 4 mL of 95% ethanol and 3.5 mL of 2 M sodium bicarbonate, at room temperature and under argon, was added 116 mg (0.1 mmole) of tetrakis (triphenylphosphine) palladium(0) and the reaction was heated at 80° C. for 2.5 hours.

After cooling to room temperature, the reaction was diluted with ethyl acetate, washed with brine (three times) and dried (MgSO$_4$), and the solvent was removed to give a clear orange oil.

This material was subjected to flash chromatography on a 75 cc column of silica gel. Elution with 50% ethyl acetate—hexane, followed by 75% ethyl acetate - hexane afforded 227 mg (0.47 mmole, 47%) of compound C as a viscous oil.

D. N-(3,4-Dimethyl-5-isoxazoly) -4'-(3-hydroxy-2-methylpropyl) [1,1'-biphenyl]-2-sulfonamide, lithium salt A solution of 220 mg (0.45 mmole) of compound C in 4 mL of ethanol and 6 mL of 6 N HCl was heated at reflux for 3 hours.

The reaction was evaporated to near dryness and the residue rendered alkaline with saturated sodium bicarbonate and washed with ether (twice). The aqueous layer was acidified with 1 N HCl and extracted with ether (twice). The organic layers were washed with brine (twice) and dried (MgSO$_4$), and the solvent was removed to yield 96 mg of crude title compound.

The ether washes of the alkaline solution remaining from above were washed with brine and dried, and the solvent was removed to give 50 mg of unreacted compound C. This material was taken into 1 mL each of ethanol and 6 N HCl and refluxed an additional 2 hours. Workup as described afforded an additional 38 mg of crude title compound.

The combined product was subjected to flash chromatography on a 60 cc column of silica gel. Elution with 2% methanol—trichloromethane afforded 113 mg (0.32 mmole) of the title compound as a white foam. This material was dissolved in methanol and 13.5 mg (0.32 mmole) of LiOH* H$_2$O added. The resulting solution was evaporated to dryness and the residue chromatographed on a 30 cc column of HP-20 resin. Elution with a step-gradient of 100% water to 50% methanol—water gave 76 mg (0.19 mmole, 42%) of the title compound as its lithium salt. M.p.: 150–160° d (dried: 60° C., high vac, overnight). Ms: (M+H)$^+$401$^+$ Calculated for C$_{21}$ H$_{23}$ N$_2$O$_4$S Li* 2.10 H$_2$O: C, 56.78; H, 6.17. Found: C, 56.98; H, 5.99.

EXAMPLE 10

4'-(1,1-Difluoro-2-methylpropyl)-N-(3,4-dimethyl-5-isoxazolyl) [1,1'-biphenyl]-2-8sulfonamide

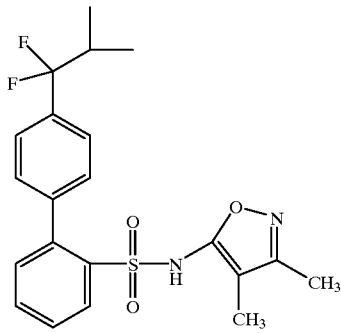

A. 4-Bromo-a-(1-methylethyl)benzenemethanol

To a solution of 9.0 g (0.048 mol) of 4-Bromobenzaldehyde in 150 mL of ether at 0° C. under argon, 2.0 M solution of isopropyl magnesium chloride in ether (29.2 mL) was added and stirred for 30 minutes. The solution was slowly warmed up to room temperature and stirred for an additional 4 hours. The mixture was then added to 150 mL of aqueous saturated sodium bicarbonate and extracted with 200 mL of ether. The organic extract was washed once with water, dried and evaporated to afford 9.8 g (95%) of the product as a gum.

B. 1-(4-Bromoahenyl)-2-methyl-1-propanone

To a 2.0 M solution of oxalyl chloride in dichloromethane (58.6 mL) at -78° C. under argon, 100 mL of dry dichloromethane was added followed by dimethylsulfoxide (18.75 g). The mixture was stirred for 10 minutes and then 9.8 g (0.0456 mol) of compound A in 100 mL of dichloromethane was added and stirred for 3 hours. Triethylamine (24 g, 0.23 mol) was then added to the mixture and stirred at -78° C. for 5 minutes. The mixture was slowly warmed to room temperature and stirred for 15 minutes. The mixture was then poured into 500 mL of 1N aqueous HCl and the organic layer was separated. The aqueous layer was back extracted with 2×100 mL of dichloromethane and the combined organic extracts were washed once with water, dried and evaporated. The residue was chromatographed on 500 g of silica gel using hexanes to afford 5.5 g (57%) of the product as a colorless liquid.

C. 1-Bromo-4-(1,1 -difluoro-2-methylpropyl)benzene

To a flask containing 2.5 g (11.85 mmol) of compound B, diethylaminosulfur trifluoride (4.2 g, 26.05 mmol) was added and the mixture was stirred at 50° C. for 48 hours. The solution was then warmed up to 70° C. to complete the reaction and then the mixture was poured into 100 mL of ice water and extracted with 2×50 mL dichloromethane. The combined organic extracts were washed once with water, dried and evaporated. The brown liquid thus obtained was distilled in vacuo to provide 1.9 g (64%) of the product as a colorless liquid. B.p. 124° C. (10–12 mm).

D. 4'-(1,1-Difluoro-2-methylproyl)-N-(3,4-dimethyl-5-isoxazolyl) -N- [(2-methoxyethoxy)-methyl][1,1'-biphenyl]-2-sulfonamide To a solution of 0.486 g (1.26 mmol) of compound C from Example 8 and 0.146 g (0.126 mmol) of tetrakis (triphenylphosphine)palladium(0) in 10 mL of toluene under argon, 8 mL of 2M aqueous sodium carbonate was added followed by 0.35 g (1.40 mmol) of compound C above added in 8 mL of 95% ethanol. The mixture was refluxed for 3 hours, diluted with 100 mL of water and extracted with 3×75 mL of ethyl acetate. The combined organic extracts were washed once with 100 mL of brine, dried and evaporated. The residue was chromatographed on 20 g of silica gel using Hexanes/ethyl acetate 3:1 to afford 0.19 g (30%) of compound D as a colorless gum.

E. 4'-(1,1-Difluoro-2-methylpropyl)-N-(3,4-dimethyl-5-isoxazolyl) [1,1'-biphenyl]-2-sulfonamide To a solution of 0.13 g (0.255 mmol) of compound D in 5 mL of dichloromethane at -78° C. under argon, 1.0 M boron tribromide in dichloromethane (0.3 mL) was added and stirred for 1 hour. The solution was slowly warmed up to room temperature and stirred for an additional 3 hours. The mixture was then diluted with 50 mL of dichloromethane, washed once with water, dried and evaporated to afford 0.16 g of the product as a colorless gum. This material was chromatographed on 25 g of silica gel using 3:1 Hexanes/ethyl acetate to provide 0.06 g (56%) of the title compound as an amorphous light brown foam. M.p.52–58° C.

Analysis Calculated For $C_{21}H_{22}F_2N_2O_3S$.: C,59.99; H,5.27; F,9.04; N,6.66; S,7.62; Found C,59.73; H,4.97; F,9.26; N,6.42; S,7.70.

EXAMPLE 11

4'-(Difluoromethoxy)-N-(3,4-dimethyl-5-isoxazolyl) [1,1'-biphenyl]-2-sulfonamide

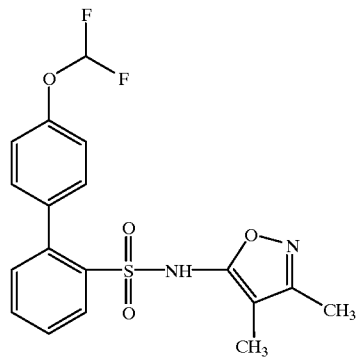

A. 1-Bromo-4-(difluaromethoxy)benzene

To 4-bromophenol (10.38 g, 60 mmol) in 36 mL $H_2O$, NaOH (2.4 g, 60 mmol) was added and the mixture was stirred at room temperature. When the mixture turned clear, 60 mL acetone was added. The reaction was heated at 50° C. and bubbled with chlorodifluoromethane gas through an inlet tube. The reaction mixture was concentrated and 300 mL hexane and 50 mL ethyl acetate were added. The organic liquid was separated and washed with 3×50 mL 1N NaOH, 50 mL $H_2O$ and 50 mL brine, dried and concentrated to give compound A (3.6 g, 27%) as a colorless liquid.

B. 4'-(Difluoromethoxy)-N-(3,4-dimethyl-5-isoxazolyl) -N-[(2-methoxyethoxy)-methyl][1,1'-biphenyl]-2-sulfonamide To a solution of compound C from Example 8 (275 mg, 0.72 mmol), compound A (479 mg, 2.15 mmol) in 6.5 mL of toluene and 5.2 mL of 95% ethanol under argon, tetrakis (triphenyl-phosphine) palladium(0) (83 mg, 0.072 mmol) was added and followed by 3.9 mL of 2M aqueous sodium carbonate. The reaction mixture was heated at 75° C. for 2 hours 40 minutes, cooled and diluted with 40 mL of ethyl acetate. The organic liquid was separated and washed with 10 mL $H_2O$ and 10 mL brine, dried and concentrated. The residue was chromatographed on silica gel using 4:1 hexane/ ethyl acetate to afford compound B (104 mg, 30%) as a colorless gum. $R_f$=0.25, silica gel, 2:1 Hexane/ethyl acetate.

C. 4'-(Difluoromethoxy)-N-(3,4-dimethyl5-isoxazolyl) [1,1'-biphenyl]-2-sulfonamide To a solution of compound B (100 mg, 0.21 mmol) in 10 mL of 95% ethanol, 10 mL of 6N aqueous HCl was added and refluxed for 1 hour. The reaction mixture was concentrated and 40 mL ethyl acetate were added. The organic liquid was washed with 10 mL $H_2O$ and 10 mL of brine, dried and concentrated. The residue was chromatographed on silica gel using 2:1 hexane/ethyl acetate to afford the title compound (51 mg, 62%) as white solid. M.p. 107–110° C.

Analysis calculated for $C_{18}H_{16}N_2O_4SF_2$: Calculated: C, 54.82; H, 4.09; N. 7.10; S, 8.13; F, 9.63; Found: C, 54.76; H, 3.86; N, 6.96; S, 8.27; F, 9.98.

EXAMPLE 12

N-(3,4-Dimethyl-5-isoxazolyl)-2'-[(formylamino) methyl]-4'-(2-methylpropyl)[1,1'-biphenyl]-2-sulfonamide

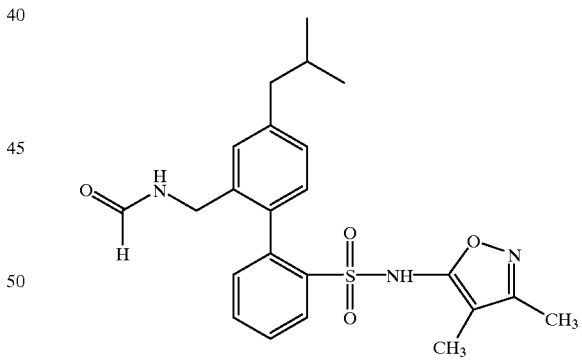

A. Acetic formic anhydride

Compound A was prepared as described in *Organic Syntheses*, Coll. Vol 6, 8–9 (1988).

B. N-(3,4-Dimethyl-5-isoxazolyl)-2'-[(formylamino) methyl]-4'-(2-methylpropyl)[1,1 '-biphenyl]-2-sulfonamide To a solution of the title compound from Example 6 (48 mg, 0.12 mmol) in 0.58 mL dichloromethane, compound A (41 mg, 0.47 mmol) was added and followed by triethylamine (47 mg, 0.47 mmol). The mixture was stirred at room temperature overnight, diluted with 30 mL dichloromethane, washed with 5 mL 0.2N hydrochloride and 0.5 mL $H_2O$ dried and concentrated. The residue was chromatographed on silica gel using 100:2.5 dichloromethane/methanol to afford a solid which was further purified by preparative HPLC on a 30×500 mm ODS S10 column using 72% solvent A (90% methanol, 10% H$_2$O, 0.1% TFA) and 28% solvent B (10% methanol, 90% H$_2$O, 0.1% TFA) to provide the title compound (40 mg, 77%) as a white solid. M.p. 78–83° C. (amorphous).

Analysis calculated for C$_{23}$H$_{27}$N$_3$O$_4$S* 0.36 H$_2$O: Calculated: C, 61.67; H, 6.24; N, 9.38; S, 7.16; Found: C, 61.81; H, 6.06; N, 9.24; S, 6.88.

EXAMPLE 13

N-(3,4-Dimethyl-5-isoxazolyl)-4'-(trifluoromethyl) [1,1'-biphenyl]-2- sulfonamide

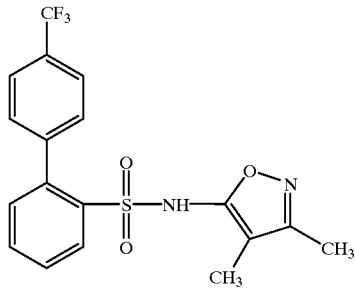

A. N-(3,4-Dimethyl-5-isoxazolyl)-N-[(2-methoxyethoxy) methyl]-4'-(trifluoromethyl)-[1,1'-biphenyl]-2-sulfonamide To a solution of 2-Bromo-N-(3,4-dimethyl-5-isoxazolyl)-N'-(methoxyethoxy-methyl)benzenesulfonamide (335 mg, 0.8 mmol, prepared as described for compound A from Example 4 of EP Publication number 0,569,193) 4-trifluoromethylbenzeneboronic acid (228 mg, 1.2 mmol) in 6.5 mL of toluene and 5.2 mL of 95% ethanol under argon, tetrakis(triphenylphosphine)palladium(0) (55 mg, 0.048 mmol) was added and followed by 3.9 mL of 2M aqueous sodium carbonate. The reaction mixture was heated at 80° C. for 4 hours, cooled and diluted with 30 mL of ethyl acetate. The organic liquid was seperated and washed with 10 mL H$_2$O and 10 mL of brine, dried and concentrated. The residue was chromatographed on silica gel using 4:1 hexane/ ethanol to afford compound A (230 mg, 59%) as a colorless gum. R$_f$ =0.42, silica gel, 2:1 Hexane/ethyl acetate.

B. N-(3,4-Dimethyl-5-isoxazolyl)-4'-(trifluoromethyl) [1.,1-biphenyl]-2-sulfonamide To a solution of compound A (230 mg, 0.48 mmol) in 8 mL of 95% ethanol, 8 mL of 6 N aqueous HCl was added and refluxed for 2 hours. The reaction mixture was concentrated to about 8 mL and extracted with 3×15 mL of ethyl acetate. The organic extracts were washed with 10 mL of brine, dried and concentrated. The residue was chromatographed on silica gel using 2:1 hexane/ethyl acetate to provide the title compound (165 mg, 88%) as a white solid. M.p. 57–62° C. (amorphous).

Analysis calculated for C$_{18}$H$_{15}$N$_2$O$_3$SF$_3$. 0.14 H$_2$O: Calculated: C, 54.21; H, 3.86; N, 7.02; S, 8.04; F, 14.29; Found: C, 54.35; H, 3.58; N, 6.88; S, 7.85;

F, 14.65.

EXAMPLE 14

N-(3,4-Dimethyl-5-isoxazolyl)-4'-(1,2,2,2-tetrafluoroethyl) [1,1'-biphenyl]-2-sulfonamide, lithium salt

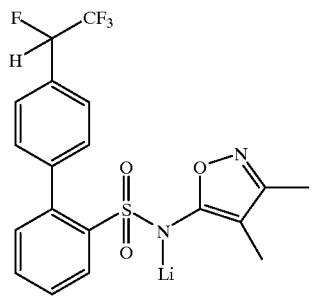

A. 1-(4-Bromorhenyl)-2,2,2-trifluoro-1-ethanone

Dibromobenzene (6.0 g, 0.025 mol) was dissolved in 59 mL of anhydrous tetrahydrofuran in a flame-dried flask. The solution was cooled to -78° C. in a dry ice/acetone bath and n-butyllithium (2.56 M in hexanes, 9.8 mL, 0.025 mol) was slowly added dropwise, keeping the reaction temperature less than -60° C. during the course of addition. Upon full addition, the reaction was stirred at -78° C. for 1 hour. The solution was then added dropwise, via cannula, to a solution of ethyl trifluoroacetate (3.56 g, 0.0257 mol) in 36 mL of ethyl ether cooled to -78° C. Upon full addition, the reaction was stirred at -70° C. for 15 minutes, and then allowed to warm gradually to room temperature. The reaction was partitioned between ethyl ether and saturated aqueous ammonium chloride, adjusting the pH of the aqueous phase to approximately pH=2 by the dropwise addition of 1 M HCl. The organic phase was washed with brine and dried over MgSO$_4$, filtered and concentrated to provide 10 g (>100%) of crude compound A which was used in the next reaction without further purification.

B. 4-Bromo-α-(trifluoromethyl)benzenemethanol

Compound A (2.5 g, 9.88 mmol) was dissolved in 20 mL of absolute ethanol and the solution was cooled to 0° C. in an ice water bath. Sodium borohydride (375 mg, 9.88 mmol) was suspended in 20 mL of absolute ethanol and the suspension was slowly added to the reaction, keeping the temperature less than 2° C. Upon full addition, the ice bath was removed and the reaction was allowed to warm to room temperature and stirred for 45 minutes. The reaction was quenched by dropwise addition of 1.0 M HCl until the bubbling ceased and the solution had a pH of 2. The reaction was then partitioned between water and ethyl ether. The aqueous phase was extracted again with ethyl ether and the organic phases were dried over MgSO$_4$, filtered and concentrated using low vacuum to remove the majority of the excess ether. The remaining solution was distilled at 1 atm to remove excess ethanol and provide 2.679 g of a yellow oil. The oil was azeotroped with pentane several times to remove any residual solvents to provide 2.368 g (94%) of the compound B.

C. 1-Bromo-4-(1,2,2,2-tetrafluoroethyl)benzene

Compound B (700 mg, 2.74 mmol) was dissolved in 6.0 mL of fluorotrichloromethane and the resulting solution was cooled to -78° C. on a dry ice/acetone bath. Diethylamino-sulfur trifluoride (444 mg, 2.75 mmol) was then added dropwise to the solution, keeping the temperature less than -65° C. Upon full addition, the reaction was warmed to room temperature and stirred for 3 hours. The reaction was then quenched with water and extracted with ethyl ether. The organic phases were dried over MgSO$_4$, filtered and concentrated under low vacuum. The material was then azeotroped with pentane to provide the crude fluoride as a yellow oil which was purified by flash chromatography (silica gel, pentane). The fractions containing product were concentrated under low vacuum and then the residual solvent was distilled off at atmospheric pressure using a short-path still to provide 482 mg (68%) of the purified fluoride as a transparent oil.

D. N-(3,4-Dimethyl-5-isoxazolyl)-N-[(2-methoxyethoxy)methyl]-4'-(1,2,2,2-tetrafluoroethyl)[1'-biphenyl]-2-sulfonamide To compound C from Example 8 (718 mg, 1.87 mmol), suspended in 15 mL of a solution of 3:4:5 saturated sodium carbonate: ethanol: toluene was added compound C above, which was also dissolved in 15–20 mL of the 3:4:5 solution. Tetrakis(triphenyl-phosphine) palladium (0) (175 mg, 0.150 mmol) was then added and the reaction was heated to 80° C. on an oil bath for 3 hours. The reaction was cooled, diluted in 220 mL of ethyl acetate, and washed with 30 mL each of water and brine. The organic phase was dried over MgSO$_4$, filtered and concentrated to yield 1.36 g of a yellow oil which was purified by flash chromatography (silica gel, 75:25 ethyl acetate: hexane) to provide 498 mg (52%) of the purified biphenyl compound D.

E. N-(3,4-Dimethyl-5-isoxazolyl)-4'-(1,2,2,2-tetrafluoroethyl) [1,1'-biphenyl]-2-sulfonamide The protected amino compound D (475 mg, 0.92 mmol) was dissolved in 12 mL of absolute ethanol and then 12 mL of 6.0 M HCl was added at room temperature. The reaction was heated to 95–100° C. for 2.5 hours, cooled, diluted with water and extracted with ethyl acetate. The organic phases were combined, dried over MgSO$_4$, filtered and concentrated to provide 430 mg of the crude amine which was purified by flash chromatography (silica gel, 99:1 dichloromethane, methanol) to provide 252 mg (64%) of free the amine compound E.

F. N-(3,4-Dimethyl-5-isoxazolyl)-4'-(1,2,2,2-tetrafluoroethyl) [1,1'-biphenyl]-2-sulfonamide, lithium salt Aqueous lithium hydroxide (1.0M, 1.0 mL) was added to compound E (252 mg, 0.588 mmol) and the solution was placed on an HP-20 column, eluting with 200 mL water, followed by 200 mL each of 20% and 30% acetone: water. The fractions containing the product were concentrated to approximately 20 mL in volume, passed through a Millipore filter and lyophilized to provide 110 mg of the desired lithium salt which was further purified by an additional HP-20 column, eluting with 200 mL of water, followed by 200 mL of 30% acetone: water. The fractions containing product were concentrated and lyophilized to provide 75 mg (26%) of the title compound as a white solid. M.p. 165–180° C.

Analysis calculated for C$_{19}$H$_{15}$N$_2$O$_3$SF$_4$*Li* 1.7 H$_2$O: C, 49.07; H, 3.99; N, 6.02; S, 6.89; F, 16.34; Found: C, 48.86; H, 3.82; N, 5.95; S, 6.81; F, 16.05.

EXAMPLE 15

N-(3,4-Dimethyl-5-isoxazolyl)-4'-(1,2,2,3,3,3-hexafluoropropyl) [1,1'-biphenyl]-2-sulfonamide, lithium salt

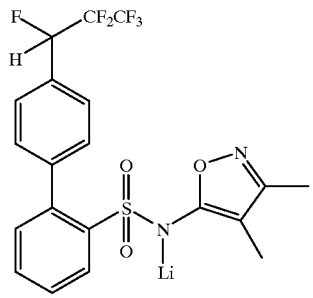

A. 1-(4-Bromophenyl)-2,2,3,3,3-pentafluoro-1-propanone

Compound A was prepared using a process analogous to the process described in Example 14A except that ethyl pentafluoropropionate (2.66 g, 13.86 mmol) was used and the crude ketone was purified by flash chromatography (silica gel, hexane). The fractions containing product were concentrated to provide 1.1 g (29%) of purified compound A as a transparent oil.

B. 4-Bromo-a-(1,1,2,2,2-pentafluoroethyl)-benzenemethanol

Compound A (890 mg, 2.94 mmol) was used in the process described in Example 14B to provide 806 mg (90%) of compound B.

C. 1-Bromo-4-(1,2,2,3,3,3-hexafluoropropyl)-benzene

Compound B (200 mg, 0.656 mmol) was used in the process described in Example 14C to provide 236 mg (>100%) of the purified compound C as a transparent oil which contained 12% by weight pentane as determined by $^1$HNMR.

D. N-(3,4-Dimethyl-5-isoxazolyl)-N-[(2-methoxyethoxy)methyl]-4'-(1,2,2,3,3,3-hexafluoropropyl) [1,1'-biphenyl]-2-sulfonamide Compound C (265 mg, 0.69 mmol) was used in a process analogous to the process of Example 14D to provide 118 mg (36%) of compound D.

E. N-(3,4-Dimethyl-5-isoxazolyl)-4'-(1,2,2,3,3,3-hexafluoropropyl) [1,1'-biphenyl]-2-sulfonamide Compound D (118 mg, 0.21 mmol) was used in a process analogous to the process of Example 14E to provide 85 mg (85%) of compound E.

F. N-(3.4-Dimethyl-5-isoxazolyl)-4'-(1,2,3,3,3-hexafluoropropyl) [1,1'-biphenyl]-2-sulfonamide, lithium salt Compound E (85 mg, 0.178 mmol) was used in a process analogous to the process of Example 14F to provide 36 mg (42%) of the desired lithium salt as a white solid. M.p. 245–260° C. $^1$H NMR (270 MHz, CD$_3$OD) δ 1.5 (d, J=3.5 Hz, 3H, CH$_3$); 2.0 (d, J=3.5 Hz, 3H, CH$_3$); 6.1 (ddd, J=43, 19, 3 Hz, 1H, CHCF$_2$CF$_3$); 7.2 (d, J=8 Hz, 1H, ArH); 7.5 (m, 6H, ArH); 8.2 (d, J=8 Hz, 1H, ArH).

What is claimed is:

1. A compound of the formula

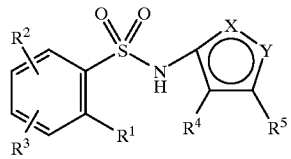

an enantiomer, diastereomer or pharmaceutically acceptable salt thereof,
wherein:
one of X and Y is N and the other is O;
$R^1$ is

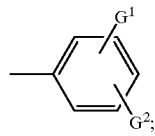

$R^2$ and $R^3$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be independently substituted with one or more of Z1, $Z^2$ and $Z^3$;
(c) halo;
(d) hydroxyl;
(e) cyano;
(f) nitro;
(g) —C(O)H or —C(O)$R^6$;
(h) —CO$_2$H or —C$_{O2}R^6$;
(i) —SH, —S(O)$_n R^6$, —S(O)$_m$—OH, —S(O)$_m$-O$R^6$, —O—S(O)$_m$-$R^6$, —O—S(O)$_m$OH or —O—S(O)$_m$-O$R^6$;
(j) —$Z^4$-N$R^7 R^8$; or
(k) —$Z^4$-N($R^{11}$)-$Z^5$-N$R^9 R^{10}$;
$R^4$ and $R^5$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be independently substituted with one or more of Z1, $Z^2$ and $Z^3$;
(c) halo;
(d) hydroxyl;
(e) cyano;
(f) nitro; (g) —C(O)H or —C(O)$R^6$; (h) —CO$_2$H or —CO$_2 R^6$; (i) —SH, —S(O)$_n R^6$, —S(O)$_m$—OH, —S(O)$_m$—O$R^6$, —O—S(O)$_m$—$R^6$, —O—S(O)$_m$OH or —O—S(O)$_m$—O$R^6$;
(j) —$Z^4$—N$R^7 R^8$;
(k) —$Z^4$—N($R^{11}$)—$Z^5$—N$R^9 R^{10}$; or
(l) $R^4$ and $R^5$ together are alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^6$ is alkyl, alkenyl, alkynyl, cycloalkyl, cycloalkylalkyl, cycloalkenyl, cycloalkenylalkyl, aryl or aralkyl, any of which may be independently substituted with one or more of $Z^1$, $Z^2$ and $Z^3$;
$R^7$, $R^8$, $R^9$, $R^{10}$ and $R^{11}$ are each independently
(a) hydrogen; or
(b) alkyl, cycloalkyl, cycloalkylalkyl, cycloalkenylalkyl, aryl or aralkyl, any of which may be independently substituted with one or more of Zl, $Z^2$ and $Z^3$;
$R^7$ and $R^8$ together may be alkylene or alkenylene, either of which may be independently substituted with one or more of $Z^1$, $Z^2$ and $Z^3$, completing a 3- to 8-membered saturated or unsaturated ring together with the nitrogen atom to which they are attached;
any two of $R^9$, $R^{10}$ and $R^{11}$ together may be alkylene or alkenylene, either of which may be independently substituted with one or more of $Z^1$, $Z^2$ and $Z^3$, completing a 3- to 8-membered saturated or unsaturated ring together with the atoms to which they are attached;
$G^1$ is
(a) hydrogen; or
(b) alkyl;
$G^2$ is
—(CH$_2$)$_m$-N$R^{12}R^{13}$ where $R^{12}$ and $R^{13}$ together are alkylene which may be independently substituted with one or more of $Z^1$, $Z^2$ and $Z^3$, completing a 3- to 8-membered saturated ring together with the nitrogen atom to which they are attached, or, together with the nitrogen atom to which they are attached form

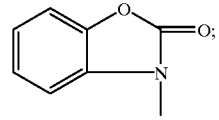

$R^{14}$ is lower alkyl substituted with 1, 2 or 3 halogen atoms;
$Z^1$, $Z^2$ and $Z^3$ are each independently
(a) hydrogen;
(b) halo;
(c) hydroxy;
(d) alkyl;
(e) alkenyl;
(f) aralkyl;
(g) alkoxy;
(h) aryloxy;
(i) aralkoxy;
(j) —SH, —S(O)$_n Z^6$, —S(O)$_m$—OH, —S(O)$_m$—O$Z^6$, —O—S(O)$_m$—$Z^6$, —O—S(O)$_m$OH or —O—S(O)$_m$—O$Z^6$;
(k) oxo;
(l) nitro;
(m) cyano;
(n) —C(O)H or —C(O)$Z^6$;
(o) —CO$_2$H or —CO$_2 Z^6$;
(p) —$Z^4$—N$Z^7 Z^8$;
(q) —$Z^4$—N($Z^{11}$)—$Z^5$—H;
(r) —$Z^4$—N($Z^{11}$)—$Z^5$—$Z^6$; or
(s) —$Z^4$—N($Z^{11}$)—$Z^5$—N$Z^7 Z^8$;
$Z^4$ and $Z^5$ are each independently (a) a single bond;
(b) —Z$^9$—S(O)$_n$—Z$^{10}$—;
(c) —Z$^9$—C(O)—Z$^{10}$—;
(d) —Z$^9$—C(S)—Z$^{10}$—;
(e) —Z$^9$—O—Z$^{10}$—;
(f) —Z$^9$—S—Z$^{10}$—;
(g) —Z$^9$—O—C(O)—Z$^{10}$—; or
(h) —Z$^9$—C(O)—O—Z$^{10}$—;

Z$^6$ is alkyl, alkenyl, alkynyl, cycloalkyl, cycloalkylalkyl, cycloalkenyl, cycloalkenylalkyl, aryl or aralkyl;

Z$^7$ and Z$^8$ are each independently hydrogen, alkyl, cycloalkyl, cycloalkylalkyl, cycloalkenylalkyl, aryl or aralkyl or Z$^7$ and Z$^8$ together are alkylene or alkenylene, completing a 3- to 8-membered saturated or unsaturated ring together with the nitrogen atom to which they are attached;

Z$^9$ and Z$^{10}$ are each independently a single bond, alkylene, alkenylene or alkynylene;

Z$^{11}$ is (a) hydrogen; or (b) alkyl, cycloalkylalkyl, cycloalkenyl, cycloalkenylalkyl, aryl or aralkyl; or any two of Z$^7$, Z$^8$ and Z$^{11}$ together are alkylene or alkenylene, completing a 3- to 8-membered saturated or unsaturated ring together with the atoms to which they are attached;

each m is independently 1 or 2; and each n is independently 0, 1, or 2.

2. The compound of claim 1, wherein R$^2$ and R$^3$ are each independently hydrogen or alkyl.

3. The compound of claim 1, wherein R$^4$ and R$^5$ are each independently alkyl.

4. The compound of claim 1, wherein R$^{12}$ and R$^{13}$, together with the nitrogen atom to which they are attached, form

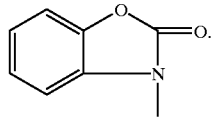

5. The compound of claim 1, wherein R$^2$ and R$^3$ are each independently hydrogen or alkyl, R$^4$ and R$^5$ are each independently alkyl, and R$^{12}$ and R$^{13}$, together with the nitrogen atom to which they are attached, form

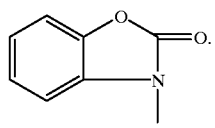

6. The compound of claim 1, wherein R$^2$ and R$^3$ are each hydrogen.

7. The compound of claim 1, wherein R$^4$ and R$^5$ are each independently alkyl of 1 to 4 carbon atoms.

8. The compound of claim 1, wherein R$^4$ and R$^5$ are each methyl.

9. The compound of claim 1, wherein R$^2$ and R$^3$ are each hydrogen and R$^4$ and R$^5$ are each independently alkyl of 1 to 4 carbon atoms.

10. The compound of claim 1, wherein R$^2$ and R$^3$ are each independently hydrogen and R$^4$ and R$^5$ are each methyl.

11. The compound of claim 1, wherein R$^2$ and R$^3$ are each hydrogen; [R$^{12}$ and R$^{13}$]R$^4$ and R$^5$ are each independently alkyl of 1 to 4 carbon atoms; and R$^{12}$ and R$^{13}$, together with the nitrogen atom to which they are attached, form

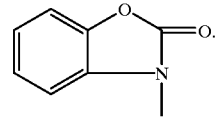

12. The compound of claim 1, wherein R$^2$ and R$^3$ are each hydrogen; R$^4$ and R$^5$ are each methyl; and R$^{12}$ and R$^{13}$, together with the nitrogen atom to which they are attached, form

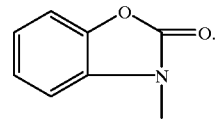

13. The compound 4'-[(2,3-Dihydro-2-oxo-3-benzoxazolyl)methyl]-N-(3,4-dimethyl-5-isoxazolyl) [1,1'-biphenyl]-2-sulfonamide.

14. A method of treating endothelin-related disorders in a mammal, which comprises administering to said mammal an effective endothelin-related disorder treating amount of a compound of claim 1.

15. A method of treating hypertension, which comprises administering an effective hypertension treating amount of a compound of claim 1.

16. A method of treating pulmonary hypertension, which comprises administering an effective pulmonary hypertension treating amount of a compound of claim 1.

17. A method of treating renal, glomerular or mesangial cell disorders, which comprises administering an effective renal, glomerular or mesangial cell disorder treating amount of a compound of claim 1.

18. A method of treating endotoxemia, which comprises administering an effective endotoxemia treating amount of a compound of claim 1.

19. A method of treating ischemia, which comprises administering an effective ischemia treating amount of a compound of claim 1.

20. A method of treating cell growth, which comprises administering an effective cell growth treating amount of a compound of claim 1.

21. A method of treating atherosclerosis, which comprises administering an effective atherosclerosis treating amount of a compound of claim 1.

22. A method of treating restenosis, which comprises administering an effective restenosis treating amount of a compound of claim 1.

23. A method of treating subarachnoid hemorrhage, which comprises administering an effective subarachnoid hemorrhage treating amount of a compound of claim 1.

24. A method of treating benign prostatic hypertrophy, which comprises administering a benign prostatic hypertrophy treating amount of a compound of claim 1.

25. A method of treating congestive heart failure in a mammal, which comprises administering to said mammal an effective congestive heart failure treating amount of a compound of claim 1.

* * * * *

UNITED STATES PATENT AND TRADEMARK OFFICE
CERTIFICATE OF CORRECTION

PATENT NO. : 6,271,248 B1
DATED : August 7, 2001
INVENTOR(S) : Murugesan et al.

It is certified that error appears in the above-identified patent and that said Letters Patent is hereby corrected as shown below:

<u>Title page,</u>
Title, should read "Substituted Biphenylsulfonamide Endothelin Antagonists"

<u>Column 32,</u>
Line 2, "[$R^{12}$ and $R^{13}$] $R^4$ and $R^5$" should read -- $R^4$ and $R^5$ --.

Signed and Sealed this

Eleventh Day of December, 2001

Attest:

NICHOLAS P. GODICI
*Attesting Officer*   *Acting Director of the United States Patent and Trademark Office*